(12) United States Patent
Clark et al.

(10) Patent No.: US 7,033,560 B2
(45) Date of Patent: Apr. 25, 2006

(54) SINGLE SOURCE MIXTURES OF METAL SILOXIDES

(75) Inventors: Robert D. Clark, Carlsbad, CA (US); Arthur Kenneth Hochberg, Solana Beach, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 101 days.

(21) Appl. No.: 10/232,052

(22) Filed: Aug. 30, 2002

(65) Prior Publication Data

US 2004/0044163 A1    Mar. 4, 2004

(51) Int. Cl.
*C01B 33/00* (2006.01)

(52) U.S. Cl. ............... 423/326; 423/269; 423/324; 423/358; 423/364; 423/411

(58) Field of Classification Search ............... 556/9, 556/27, 42, 51, 173
See application file for complete search history.

(56) References Cited

U.S. PATENT DOCUMENTS

| | | | | |
|---|---|---|---|---|
| 4,478,952 A | * | 10/1984 | Mack et al. | 502/110 |
| 5,017,695 A | * | 5/1991 | Gradeff et al. | 534/15 |
| 5,318,935 A | * | 6/1994 | Canich et al. | 502/117 |
| 5,536,857 A | * | 7/1996 | Narula et al. | 556/10 |
| 6,238,734 B1 | | 5/2001 | Senzaki et al. | 427/226 |
| 6,399,208 B1 | * | 6/2002 | Baum et al. | 428/446 |
| 6,476,245 B1 | * | 11/2002 | Cavell et al. | 556/9 |
| 2003/0104209 A1 | * | 6/2003 | Bellman et al. | 428/409 |

FOREIGN PATENT DOCUMENTS

| | | | |
|---|---|---|---|
| GB | 1428108 | * | 3/1976 |
| JP | 8-12718 A | * | 1/1996 |
| JP | 11-292890 A | * | 10/1999 |
| WO | 0125502 | | 4/2001 |
| WO | WO 01/25502 A1 | | 4/2001 |
| WO | WO 02/27063 A2 | | 4/2002 |
| WO | WO 02/079211 A | | 10/2002 |

OTHER PUBLICATIONS

"Low Temperature Pyrolytic Transformations of Tri-Tert-butoxysiloxy Derivatives of Aluminum to Aluminosilicate Materials", Tilley et al., in Chemistry of Materials 1992, 4, 1290-1295.*
"Block Copolymer-Assisted Synthesis of Mesoporous Multicomponent Oxides by Nonhydrolytic, Thermolytic Decomposition of Molecular Precursors in Nonpolar Media", Tilley et al., in Chemistry of Materials 2001, 13, 3354-3563.*

(Continued)

Primary Examiner—Marc Zimmer
(74) Attorney, Agent, or Firm—Geoffrey L. Chase

(57) ABSTRACT

This invention pertains to complex mixtures of the formula M is a metal having a valence of from 2–6, L1 is an anionic ligand and L2 is a siloxide or silyl amide ligand suited for producing stable thin-film metal silicates, v is equal to the valence of the metal, and $0<x<v$. The bonding is such that an M—O—Si or an M—N—Si linkage exists, respectively, and the stability for the complex is provided by the organic ligand. The invention also relates to a process for preparing the metal siloxide complexes.

Thus, the complexes can be represented by the formulas $$(R)_m M—(O—SiR_1R_2R_3)_n$$

and $$(R)_m M—[N—(SiR_1R_2R_3)_y(R_4)_{2-y}]_n$$

wherein M is a metal having a valence of 2–6, m and n are positive integers and m plus n is equal to the valence of the metal M. The R type groups, i.e., R, $R_1$, $R_2$, $R_3$, and $R_4$ represent an organo ligand.

15 Claims, 1 Drawing Sheet

OTHER PUBLICATIONS

"New Vanadium Tris(tert-butoxy)silocy Complexes and their Thermolytic Conversions to Vanadia-Silica Materials", Tilley et al. in Chemistry of Materials 2002, 14, 3554-3563.* abstract of JP 49-33756 B4.*

Abstract of "Novel Convenient, Low-cost Alternative Method for Film Fabrication. Titanium Nitride Thin Films of Alumina Substrates for Automotive Applications from a Molecular Precursor" in Chemical Vapor Deposition 1995, 1(2), 51-53.*

Abstract from the article entitled "A Novel Borosilicate glass (SiOB-BSG) by low pressure decomposition of a monomolecular liquid precursor" published in Journal de Physique, Colloque, (C4, 18th Eur. Solid State Device Res. Conf., 1988), C4-C541/C4 544.*

Abstract from "Preparation and Characterization of some alumosiloxanes as single-source MOCVD precursors for aluminosilicate coatings" published in Journal de Physique IV: Proceedings (2000), 10(Pr2, Chemical Vapor Deposition), Pr2/3 Pr2/42.*

Abstract from the article entitled "Reactions of Phenylethynyl and Silylamido Lanthanide Derivatives with Esters" published in Metalloorganicheskaya Khimiya (1991), 4(2), 407-410.*

Abstract from "Benzopheneone Complexes of the Lanthanides: Synthesis of [Ln{N(SiMe3)2}3(Ph2CO)] L=La, Eu, Tb, Yb, or Y) and X-ray Crystal Structure of the Terbium Complex" taken from Polyhedron (1992), 11(4), 409-413.*

Abstract for WO 2000-20462.*

Abstract for WO 2002/90394.*

"Terphenyl Ligand Systems in Lanthanide Chemistry: Synthesis and Structural Characterization of Two 2,6-dimesitylphenyl Derivatives of Trivalent Ytterbium" authored by Rabe et al. appearing inInorg Chem, 1999, 38, 3446.*

"Cerium Masquerading as a Group 4 element: Synthesis, Structure, and Computational Characterization of CECl{N (SiMe3)2}3" authored by Eisenstein et al. appearing in Chem. Commun, 2001, 1560-1561.*

"Synthesis and Structural Characterization of Several Ytterbium Bis(trimethylsily)amides including Base-free [Yb{N(SiMe3)2}2(m-Cl)]2- A Coordinateively Unsaturated Complex with Additional Agnostic Yb-(H3C-Si) Interactions" authored by Niemeyer appearing i.*

"Dibenzylzirconium Complexes of Chelating Aminodiolates. Synthesis, Structural Studies, Thermal Stability, and Insertion Chemistry" authored by Shao et al. appearing in Organometallics., 2000, 19, 509.*

"Alkoxysilanes VI. The preparation of Alkoxysilane Derivatives of Zirconium and Tin" authored by Abe et al. appearing in Bull. Chem. Soc. Jpn., 1972, 45, 1258.*

"Dialkyl Bis[bis(trimethylsilyl)amide] Group 4A Compounds. Phosphine-induced Transformation of a bridging carbene into a Metallacycle. Crystal Structure of Zr [Ch2Si(Me)2NSiMe3]2(Me2PCh2Ch2PMe2)" authored by Andersen et al. appearing in Organometallics.*

"Ketyl Complexes of (silox)3Ti(silox=t-Bu3SiO)" authored by Wolczanski et al. appearing in Inorg. Chem., 1992, 31, 66.*

"Hydrocarbon Activation via Reversible 1,2 RH Elimination from (t-Bu3SiNH)ZrR: Synthetic, Structural, and Mechanistic Investigations" authored by Wolczanski et al. appearing in J. Am. Chem. Soc., 1996, 118, 591.*

K. W. Terry, et al, "Trialkoxysiloxy Complexes as Precursors . . .", Chem. Mater. 1991, 3 1001-1003.

K.W. Terry, "Trialkoxysiloxy Complexes as Precursors to M02.4SiO2 . . . Materials," Chem. of Materials, 1991, P. 1001-1003, vol. 3.

* cited by examiner

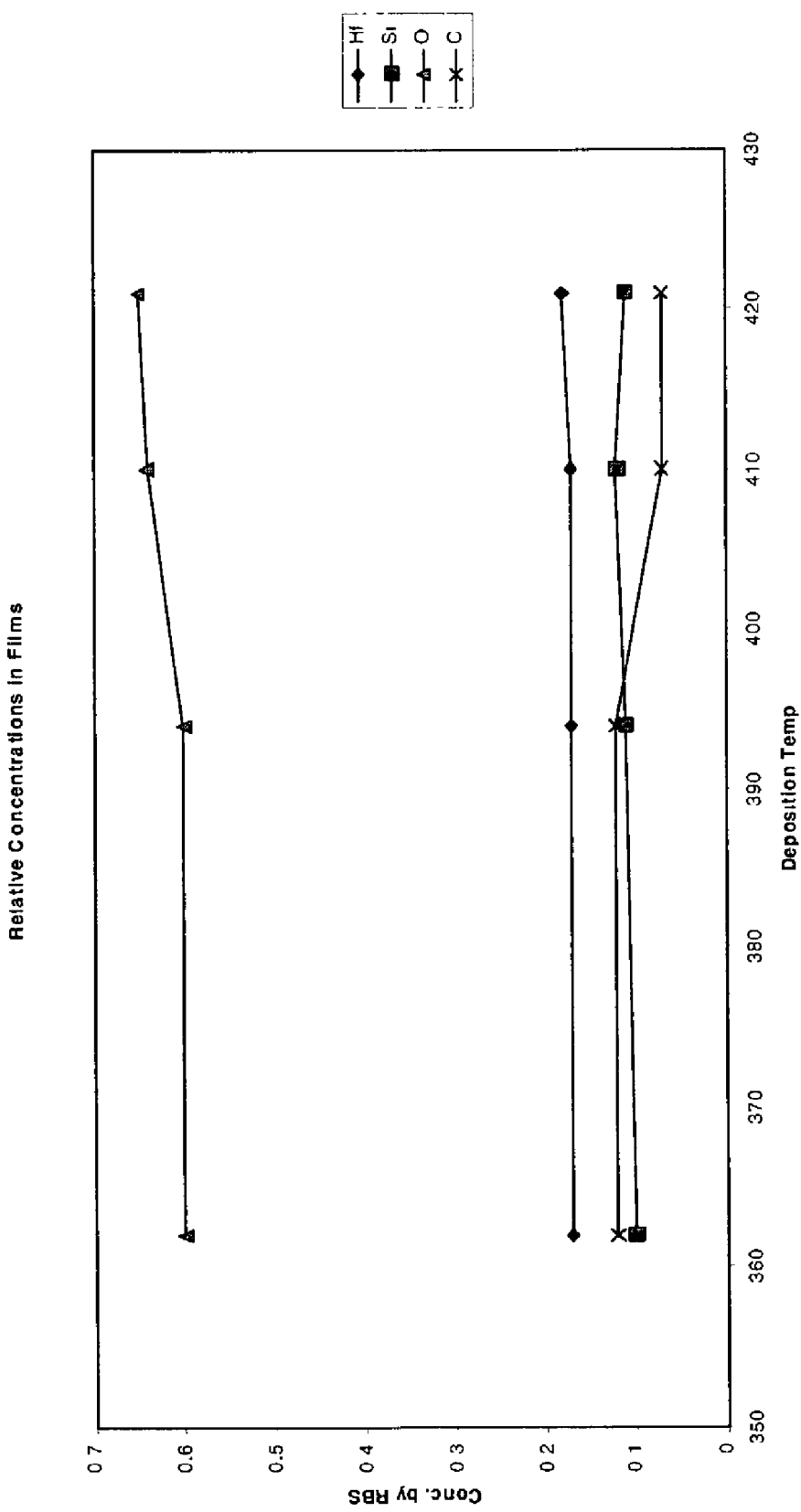
Figure

SINGLE SOURCE MIXTURES OF METAL SILOXIDES

BACKGROUND OF THE INVENTION

Chemical vapor deposition (CVD) of metal siloxides has been used to deposit stable thin-film silicates as gate dielectrics (high dielectric constant) onto silicon substrates for use in the microelectronics industry. Single source metal siloxide precursors greatly simplify production and processing. Representative single source precursors which have been used in the past include $Zr(OSiMe_3)_4$, $Zr(OSiEt_3)_4$, $Hf(OSiEt_3)_4$, $Zr[OSi(OtBu)_3]_4$, $Hf[OSi(OtBu)_3]_4$, $(thd)_2Zr(OSiMe_3)_2$, and $(thd)_2Hf(OSiMe_3)_2$.

Chemical vapor deposition of these single source metal siloxides, although simplifying some aspects in the production of thin films introduce different problems to the process and in the design of the thin-film composition. $Zr(OSiMe_3)_4$, for example, is a solid at room temperature. The compounds $(thd)_2Zr(OSiMe_3)_2$ and $(thd)_2Hf(OSiMe_3)_2$ are solids and suffer from low volatility due to the use of bulky thd ligands. Other precursors such as $Zr[OSi(OtBu)_3]_4$ and $Hf[OSi(OtBu)_3]_4$ also have been found to have relatively low volatility.

Single source metal siloxide precursors which are liquids such as $Zr(OSiEt_3)_4$ and $Hf(OSiEt_3)_4$, are preferred for thin-film applications. Although, in liquid form, they too can present problems when designing the desired composition of the resultant thin-film. The design becomes a problem because each of the previous liquid metal siloxides has a well-designed metal:Si ratio of either 1:4 (0.25) or 1:2 (0.5). For example $Zr(OSiMe_3)_4$ has a metal:Si ratio of 1:4 and $(thd)_2Zr(OSiMe_3)_2$ has a metal:Si ratio of 1:2. To achieve thin-film compositional ratios other than that produced from the pure 1:4 and 1:2 complexes, the art has employed the use of multiple sources. One technique employing secondary sources for achieving metal silicon ratios other than the fixed ratios of 1:2 and 1:4. is through the use of mixture of a silicon containing metal (zirconium) source. e.g., $Zr(OSiMe_3)_4$ and a non-silicon containing metal (zirconium) source, e.g., $Zr(OtBu)_4$ delivered either separately, as a mixture or dissolved in a solvent. Another technique is through the use of a non-metal containing compound of silicon, e.g., $Si(NMe_2)_4$ and a metal siloxide compound, e.g., $Zr(OSiMe_3)_4$ delivered either separately, as a mixture or dissolved in a solvent. Another technique uses a non-metal containing silicon compound, e.g., $Si(NMe_2)_4$ and a metal containing compound, e.g., $Zr(NEt_2)_4$ delivered either separately, as a mixture, or dissolved in a solvent.

Single source mixtures of separate complexes introduce a number of problems to the CVD process. Because the relative rate of deposition for each precursor may vary significantly with temperature and pressure due to differences in activation energy, it is difficult to uniformly control the metal:Si ratio deposited as a thin-film dielectric. The use of separate metal and silicon sources also requires delivery equipment for multiple chemical sources as well as control over the ratio in which they are delivered.

Representative patents and articles illustrating the preparation and deposition methods for single source precursors are as follows:

WO 01/25502 discloses gate dielectric films of zirconium and hafnium silicates on silicon substrates. The precursor metal compound includes a metal such as zirconium or hafnium and at least an alkoxide or β-diketonate; a second precursor not containing silicon to provide a ratio $M_x/Si_{1-x}$ of from 0.01 to 0.99. These precursors are produced by reacting a β-diketone, such as 2,2,6,6-tetramethyl-3,5-heptanedione (Hthd), with $ZrCl_2$ suspended in diethyl ether. The resulting compound then are mixed in one to two molar ratio with $LiOSiMe_3$, thereby forming $Zr(thd)_2(OSiMe_3)_2$. Deposition of a mixture of $Zr(OSiMe_3)_4$ and $Zr(OtBu)_4$ is shown.

U.S. Pat. No. 6,238,734 discloses the deposition of a metal compound or mixture of at least a two ligand complex onto substrates suited for semiconductor fabrication. A mixture of two or more metal-ligand complexes as the precursor is employed. Ligands are the same and are selected from the group consisting of alkyls, alkoxides, halides, hydrides, amides, imides, azides, nitrates, cyclopentadienyls, carbonyls, and their fluorine, oxygen and nitrogen substituted analogs. Representative metal-ligand complexes include: $Si(N(CH_2CH_3)_2)$, $Ti(N(CH_2CH_3)_2)_4$, $Zr(N(CH_2CH_3)_2)_4$, $Hf(N(CH_2CH_3)_2)_4$, $V(N(CH_2CH_3)_2)_5$, $V(N(CH_2CH_3)_2)_4$, $Nb(N(CH_2CH_3)_2)_5$, $Nb(N(CH_2CH_3)_2)_4$, $CH_3CH_2N=Nb(N(CH_2CH_3)_2)_3$, $CH_3CH_2N=V(N(CH_2CH_3)_2)_3$, $(CH_3CH_2N=)_2W(N(CH_2CH_3)_2)_2$, $(CH_3CH_2N=)_2Mo(N(CH_2CH_3)_2)_2$, and $CH_3CH_2N=Ta(N(CH_2CH_3)_2)_3$.

Terry et al in an article, *Trialkoxysiloxy Complexes as Precursors to $MO_2.4SiO_2$ (M=Ti, Zr, Hf) Materials*, Chem. Mater. 1991, 3 1001–1003 disclose chemical routes to ceramic materials based upon alkoxysiloxy transition-metal complexes as single source precursors to homogenous metal silicate networks. These complexes of the formula $M[OSi(OtBu)_3]_4$ where M=Ti, Zr, or Hf are used to produce $MO_2.4SiO_2$ materials. One type of complex is produced by refluxing a toluene solution of $HOSi(OtBu)_3$ (4 equiv) with $Ti(NEt_2)_4$.

BRIEF SUMMARY OF THE INVENTION

This invention pertains to precursor mixtures of the formula $M(L1)_x(L2)_{v-x}$ wherein M is a metal having a valence of from 2–6, L1 is an anionic ligand and L2 is a siloxide or silyl amide ligand suited for producing stable thin-film metal silicates, v is equal to the valence of the metal, and 0<x<v. The bonding is such that an M—O—Si or an M—N—Si linkage exists, respectively. The invention also relates to a process for preparing the metal siloxide and metal silyl amide precursor mixtures.

The complexes forming the mixture are more specifically represented by the formulas:

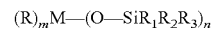

and

wherein M is a metal valence 2–6, m and n are positive integers and m plus n is equal to the valence of the metal M, and y is 1 or 2. The R type groups, i.e., R, $R_1$, $R_2$, R3, and $R_4$ represent an organic ligand. They may be like or unlike.

There are significant advantages to the metal precursor complexes described herein and their application to thin film formation such as in microelectronic circuits.

an ability to formulate metal/siloxane complexes at preselected ratios of M:Si;

an ability to formulate single source precursors for use in deposition processes such as CVD;

an ability to eliminate the processing difficulties associated with physical mixtures of single source precursors; e.g., those difficulties associated with different rates of deposition, different deposition temperatures; and compositional variations; and, an ability to produce single source precursors having a definite metal:Si ratio which are relatively insensitive to deposition temperature and pressure changes due to the fact the individual complexes of the single source precursor mixture have similar activation energies and, therefore, similar relative rates of deposition at a variety of temperatures.

BRIEF DESCRIPTION OF THE DRAWING

The FIGURE is a graph of concentrations of various identified elements in deposited films as a function of temperature.

DETAILED DESCRIPTION OF THE INVENTION

This invention relates to a single source metal siloxide precursor mixtures of the form $M(L1)_x(L2)_{v-x}$ wherein M is a metal having a valence or from 2–6, typically Zr, Ti of Hf when used in microelectronic applications, L1 is an anionic ligand and L2 is a siloxide or silyl amide ligand suited for producing stable thin-film metal silicates, v is equal to the valence of the metal, and $0<x<v$. The resultant mixtures contain metal complexes in which an anionic silicon-containing moiety is bound to the metal through an oxygen or nitrogen atom such that a M—O—Si or M—N—Si linkage exists.

As source reagents for metal organic chemical deposition (MOCVD) and the preparation of the precursor, Group 2–6 metals are suited for the synthesis of the metal siloxides and silyl amides. Representative metals and lanthanides include aluminum, gallium, indium, thallium, tin, lead, antimony, bismuth, beryllium, magnesium, calcium, strontium, barium, scandium, yttrium, lanthanum, titanium, zirconium, hafnium, vanadium, niobium, tantalum, chromium, molybdenum, tungsten, manganese, technetium rhenium, iron, ruthenium, osmium, cobalt, rhodium, iridium, nickel, palladium, platinum, copper, silver, gold, cerium, praseodymium, neodymium, samarium, europium, gadolinium, terbium, dysprosium, holmium, erbium, thulium ytterbium, lutetium, actinium, thorium, protactinium and uranium. Preferably, the metals employed in the synthesis of metal siloxides and silylamides for microelectronic applications are the Group 4 metals, zirconium, hafnium, and titanium and the Group 5b metals niobium, tantalum and vanadium. For some applications the Group 3 metals aluminum, gallium, indium and thallium are preferred.

Ligands L1 and L2 in the formula $M(L1)_x(L2)_{v-x}$ and represented by the R type groups, R, $R_1$, $R_2$, $R_3$, and $R_4$ in the formulas;

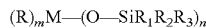

and

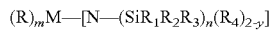

can be monodentate or polydentate and include $C_{1-8}$ alkyl, $C_{1-8}$ alkoxides, benzyl, halides, hydrides, amides, imides, azides, nitrates, cyclopentadienyls, carbonyls, and their fluorine, oxygen and nitrogen substituted analogs, a β-diketonate, and $N(R_5)_2$ where $R_5$ is $C_{1-8}$ alkyl, $C_{1-8}$ alkoxide, $C_{1-8}$ dialkylamino and benzyl. As is known the type of R—$R_5$ groups in a single source metal siloxide precursor have an effect on the properties of the resultant metal siloxide. R groups should be selected to provide the type of properties desired for the deposition process employed. Liquid single source metal siloxide and silyl amide precursors, often use non-bulky groups, e.g., methyl, ethyl and so forth. Crown ethers and β-diketones such as 2,4-pentanedione sometimes referred to herein as hexafluoroacetylacetone and 2,2,6,6-tetramethylheptane-3,5-dione can be used.

Specific examples of $C_{1-8}$ alkyl include methyl, ethyl, i-propyl and t-butyl; benzyl, the $C_{1-8}$ alkoxides, e.g., methoxy, ethoxy, propoxy, and i-butoxy, s-butoxy, t-butoxy; ethers such as methyl ether, diethyl ether, phenyl ether and so forth; amides such as formamide, acetamide and benzamide, dimethyl amido, diethyl amido, ethylmethyl amido, butyl amido, dipropyl amido, methylpropyl amido, ethylpropyl amido; and amines such as dimethylamine, diethyl amine. It is important to use the same or common ligands, homoleptic ligands, to avoid potential ligand exchange problems of the prior art.

Metal siloxides are preferred to metal silyl amides due to their greater ease of oxidation and lesser steric bulk. In addition, the preferred metal siloxide precursor complexes are room temperature liquids with sufficiently low viscosity to allow the use of neat liquid source delivery without incorporating solvents or heated source containers or delivery lines prior to vaporization.

The metal siloxide single source complexes are typically but not exclusively derived from the reaction of a metal oxide complex and a silanol including but not limited to silane-diols and -triols. Sometimes these silanols are considered Si analogs of alkoxides. Examples of silane diols and silane triols suited for producing the metal siloxides include: $C_{1-8}$ alkyl silanols, such as trimethylsilanol, triethyl silanol, tri-i-and n-propyl silanol, and t-butyl silanol.

Silyl amides are similar to siloxides, but incorporate N in place of O. Silyl amides are typically but not exclusively derived from silyl amines including by not limited to disilyl amines such as hexamethyldisilazane (HMDS).

One method for preparing the metal siloxide precursor complex is to react a group 2–6 metal complex of the formula $M(OR)_v$ with a silanol of the formula HO—Si$(R_1R_2R_3)$. The metal oxide complex and the silanol or silyl amide may be reacted in various molar ratios leading to various metal to silicon mole ratios, the excess ligands providing the stabilizing influence. Because there is an excess of ligand, the M:Si ratios may vary slightly within a given composition. For purposes of composition design, the composition is assumed to be approximately in proportion to the mole ratio in which they are reacted. Also, because of these differences, the single metal siloxide or metal silylamide species is an intimate mix of metal complexes having preselected M:Si ratios of 1:X where $0<x<v$.

A solvent may be used to form the metal siloxides or metal silyl amides. Typically, the silanols or silyl amines employed to form the complex are dissolved in an appropriate solvent to produce crude versions of the aforementioned mixtures. Examples of solvents include: hydrocarbons such as hexane, octane and the like, ethers such as tetrahydrofuran and so forth.

Purification of the reaction product is accomplished by removal of the solvent under vacuum and by distillation. The purified mixture is characterized by NMR spectrometry and GC-MS. The actual compositions of the metal siloxide and metal silylamide complexes may be determined analytically using either NMR, GC-MS or some other equivalent analytical technique. The reaction product will contain detectable quantities of at least two separate complexes with different values of x such that the difference between the individual values of x is 1.

Examples of metal complex mixtures that can be produced by the process include: $[(CH_3CH_2)_2N]_mZr[OSi(CH_2CH_3)_3]_n$; $[(CH_3CH_2)_2N]_mHf[OSi(CH_2CH_3)_3]_n$, $[(t-C_4H_9)O]_mZr[OSi(CH_2CH_3)_3]_n$, and $[(t-C_4H_9)O]_mHf[OSi(CH_2CH_3)_3]_n$. The value of m and n will be greater than 0 and less than 4 and m plus n is equal to 4 in these mixtures.

Chemical vapor deposition of the complexes to form thin metal silicate films, e.g., Zr and Hf silicate films with definite Zr:Si and Hf:Si ratios based upon the empirical formula may be accomplished by bringing the source into contact with a substrate as a liquid or in the vapor phase with a heated substrate (100–700° C.). Silicon wafers are the substrate of choice. Other methods of deposition include ALCVD, MBE, spin-on and misted vapor deposition.

The following examples are provided to illustrate various and preferred embodiments of the invention and are not intended to restrict the scope thereof.

EXAMPLE 1

Synthesis of a Precursor Having the Empirical Composition $Hf(NEt_2)_{3.15}(OSiEt_3)_{0.85}$ The synthesis of a precursor having the empirical composition $Hf(NEt_2)_{3.15}(OSiEt_3)_{0.85}$ is achieved by the following process All manipulations were carried out in the absence of moisture and air under nitrogen or argon using standard Schlenk and glovebox techniques. In the glovebox, $Hf(NEt_2)_4$(75.71 g, 162.3 mmol) was weighed into a 500 mL Schlenk flask equipped with a stir bar. Hexane (~200 mL) was added to the flask. A pressure-equalizing addition funnel containing $HOSiEt_3$ (21.3 g, 161 mmol) and hexane (~50 mL) was attached to the flask and capped with a septum. The reaction apparatus was removed from the glovebox and attached to a Schlenk line.

Prior to introduction of reactants, the reaction flask was placed in a dry ice/isopropanol bath. A silanol solution was added dropwise to the reaction mixture over a period of 30 to 45 minutes. Stirring was continued overnight as the flask and bath were allowed to warm to room temperature to complete the reaction.

After completion of the reaction, the addition funnel was removed and replaced with a septum. The solvent was then removed under vacuum over a period of about 5 hours. The resulting liquid was vacuum distilled to yield 57 g of a single source precursor having the empirical composition $Hf(NEt_2)_{3.15}(OSiEt_3)_{0.85}$ leading to an Hf/Si ratio of 3.7 by NMR spectrometry as a light yellow liquid. The precursor was characterized by $^1H$ and $^{13}C$ NMR and by GC-MS. Both $Hf(NEt_2)_4$(m/z 468) and $Hf(NEt_2)_3(OSiEt_3)$ (m/z 527) were detected by GC-MS. $^1H$ NMR was used to establish the empirical composition since the decomposition products diethylamine and hexaethyldisiloxane were both detected by GC-MS, indicating some decomposition on the column. The $^{13}C$ NMR spectrum indicates the presence $Hf(NEt_2)_4$, $Hf(NEt_2)_3(OSiEt_3)$, and $Hf(NEt_2)_2(OSiEt_3)_2$ as well.

EXAMPLE 2

Synthesis of a Precursor Having the Empirical Composition $Hf(NEt_2)_{1.66}(OSiE_3)_{2.34}$ The synthesis of a precursor having the empirical composition $Hf(NEt_2)_{1.66}(OSiEt_3)_{2.34}$ was achieved by the following process. All manipulations were carried out in the absence of moisture and air under nitrogen or argon using standard Schlenk and glovebox techniques. In the glovebox, $Hf(NEt_2)_4$(74.96 g, 160.7 mmol) was weighed into a 500 mL Schlenk flask equipped with a stir bar. Hexane (~100 mL) was added to the flask. A pressure-equalizing addition funnel containing $HOSiEt_3$(47.5 g, 359 mmol) and hexane (~50 mL) was attached to the flask and capped with a glass stopper. The reaction apparatus was removed from the glovebox and attached to a Schlenk line.

While cooling the reaction flask in a dry ice/isopropanol bath the silanol solution was added dropwise to the reaction mixture over a period of about 15 minutes. Stirring was continued overnight as the flask and bath were allowed to warm to room temperature. The addition funnel was removed and replaced with a septum. The solvent was then removed under vacuum over a period of about 8 hours. The resulting liquid was vacuum distilled to yield 63 g of a precursor having the empirical composition $Hf(NEt_2)_{1.66}(OSiEt_3)_{2.34}$ leading to an Hf/Si ratio of ~0.70 by NMR spectrometry as a light orange liquid. The precursor was characterized by $^1H$ and $^{13}C$ NMR. Integration of the $^1H$ NMR spectrum was used to establish the empirical composition. The $^{13}C$ NMR spectrum indicates the presence $Hf(NEt_2)_3(OSiEt_3)$, $Hf(NEt_2)_2(OSiEt_3)_2$, and $Hf(NEt_2)(OSiEt_3)_3$ as well.

EXAMPLE 2

Synthesis of a Precursor Having the Empirical Composition $Hf(OtBu)_{3.30}(OSiEt_3)_{0.70}$ The synthesis of a precursor having the empirical composition $Hf(OtBu)_{3.30}(OSiEt_3)_{0.70}$ (an Hf/Si ratio of ~4.7 was effected by the following process. All manipulations were carried out in the absence of moisture and air under nitrogen or argon using standard Schlenk and glovebox techniques. In the glovebox, $Hf(OtBu)_4$ (81.80 g, 173.7 mmol) was weighed into a 500 mL Schlenk flask equipped with a stir bar. Hexane (~200 mL) was added to the flask. A pressure-equalizing addition funnel containing $HOSiEt_3$ (23.01 g, 173.9 mmol) and hexane (~10 mL) was attached to the flask and capped with a glass stopper. The reaction apparatus was removed from the glovebox and attached to a Schlenk line.

While cooling the reaction flask in a dry ice/isopropanol bath the silanol solution was added dropwise to the reaction mixture over a period of about 50 minutes. Stirring was continued overnight as the flask and bath were allowed to warm to room temperature. The addition funnel was removed and replaced with a septum. The solvent was then removed under vacuum over a period of about 10 hours. The resulting yellow cloudy liquid was vacuum distilled to yield 73.45 g of a precursor having the empirical composition $Hf(OtBu)_{3.30}(OSiEt_3)_{0.70}$ by NMR spectrometry as a clear colorless liquid. The precursor was characterized by $^1H$ and $^{13}C$ NMR. Integration of the $^1H$ NMR spectrum was used to establish the empirical composition. NMR spectra indicate the presence of both $Hf(OtBu)_4$ and $Hf(OtBu)_3(OSiEt_3)_1$.

EXAMPLE 4

Chemical Vapor Deposition of Hf Silicate Films

Chemical vapor deposition of Hf silicate films from a precursor having the empirical composition $Hf(NEt_2)_{1.66}(OSiEt_3)_{2.34}$. The liquid precursor was transported via liquid delivery to a vaporizer and delivered to a CVD reaction chamber. The precursor was reacted at a heated substrate (200–800° C.) in a oxidizing environment to produce Hf silicate films. Si/Hf ratios based upon the empirical formula of the complex were between 0.62 and 0.71 in the resulting films as determined by RBS. The Si/Hf ratios were relatively insensitive to deposition temperature.

The chart in the FIGURE shows that the Si:Hf mole ratio in the resultant film does not vary significantly with temperature. Thus, differences in heating across a wafer will not result in compositional gradients across the wafer, which is critical to ensure device performance. As the semiconductor industry trends toward larger substrate sizes this advantage becomes even more pronounced over the use of physical mixtures of disparate compounds as precursors.

The present invention has been set forth with regard to several preferred embodiments, but the scope of the present invention should be ascertained from the claims which follow.

The invention claimed is:

1. A metal siloxide precursor which is composed of a complex represented by the empirical formula:

$$(R)_mM\text{---}(O\text{---}SiR_1R_2R_3)_n$$

wherein M is a Group 4 metal selected from the group consisting of zirconium and hafnium; R is $(CH_3CH_2)_2N$ and $R_1$ $R_2$ and $R_3$ are ethyl; and m plus n is equal to a valence of the M metal (v).

2. A metal siloxide or silyl-amide precursor which are composed of complexes represented by the empirical formulas:

$$(R)_mM\text{---}(O\text{---}SiR_1R_2R_3)_n$$

and $$(R)_mM\text{---}[N\text{---}(SiR_1R_2R_3)_y(R_4)_{2-y}]_n$$

wherein M is a metal selected from the group consisting of Sc, Y, La, Pr, Nd, Sm, Eu, Gd, Tb, Dy, Ho, Er, Tm, Yb, and Lu; $R_1$ $R_2$ $R_3$ and $R_4$ are monodentate or polydentate ligands selected from the group consisting of $C_{1-8}$ alkyl, $C_{1-8}$ alkoxides, benzyl, ethers, halides, hydrides, amides, imides, azides, nitrates, cyclopentadienyls, carbonyls, a β-diketonate, and $N(R_5)_2$ wherein $R_5$ has the same meaning as $R_1$ $R_2$ $R_3$ and $R_4$ and their fluorine, oxygen and nitrogen substituted analogs; R is a monodentate or polydentate ligand selected from the group consisting of $C_{1-8}$ alkyl, $C_{1-8}$ alkoxides, benzyl, halides, hydrides, amides, azides, nitrates, cyclopentadienyls, a β-diketonate, and $N(R_5)_2$ wherein $R_5$ has the same meaning as $R_1$ $R_2$ $R_3$ and $R_4$ and their fluorine, oxygen and nitrogen substituted analogs, m and n are positive numbers and m plus n is equal to the valence of the M metal (v), and y is either 1 or 2.

3. The metal siloxide or silyl-amide precursor complex of claim 2 wherein the β-ketonate is derived from 2,4-pentanedione, and 2,2,6,6-tetramethylheptane-3,5-dione.

4. The metal siloxide or silyl-amide precursor complex of claim 2 wherein R, $R_1$ $R_2$ $R_3$ and $R_4$ are selected from methyl, ethyl, i-propyl and t-butyl; methyl ether, diethyl ether, phenyl ether; methoxy, ethoxy, propoxy, i-butoxy, s-butoxy, and t-butoxy, dimethylamido, and diethylamido.

5. A metal silyl-amide precursor complex which is represented by the formula:

$$(R)_mM\text{---}[N\text{---}(SiR_1R_2R_3)_y(R_4)_{2-y}]_n$$

wherein M is selected from the group consisting of hafnium and zirconium, R is t-butoxy or diethylamido or dimethylamido, and $R_1$ $R_2$ $R_3$ and $R_4$ are methyl or ethyl; and m plus n is equal to the valence of the metal (v) and y is either 1 or 2.

6. A process for producing a metal siloxide precursor complex which is represented by the empirical formula:

$$(R)_mM\text{---}(O\text{---}SiR_1R_2R_3)_n$$

wherein M is a metal selected from the group consisting of hafnium and zirconium; R t-butoxy, diethylamido, or dimethylamido and $R_1$, $R_2$, and $R_3$ are ethyl; and m plus n is equal to the valence of the metal (v), which comprises the step:

(a) reacting a metal complex of the formula $M(R)_4$ has the meaning recited above with a silanol of the formula HO—Si—$R_1$ $R_2$ $R_3$ wherein $R_1R_2$ and $R_3$ have the meanings recited above.

7. A metal siloxide precursor mixture of the formula $Hf(O-t-Bu)_m(OSiEt_3)_n$ where m and n are positive numbers and m plus n is equal to four and hafnium is in the +4 oxidation state.

8. A metal siloxide precursor mixture of the formula $Hf(NEt_2)_m(OSiEt_3)_n$ where m and n are positive numbers and m plus n is equal to four and hafnium is in the +4 oxidation state.

9. A metal siloxide precursor which comprising a complex represented by the empirical formula:

$$(R)_mM\text{---}(O\text{---}SiR_1R_2R_3)_n$$

wherein M is a metal having a valence number v and selected from the group consisting of Zr, Hf, Sc, Y, La, Pr, Nd, Sm, Eu, Gd, Tb, Dy, Ho, Er, Tm, Yb, and Lu; $R_1$, $R_2$, $R_3$, and $R_4$ are each independently monodentate or polydentate ligands selected from the group consisting of $C_{1-8}$ alkyl, $C_{1-8}$ alkoxide benzyl, hydrides, amides, azides, nitrates, cyclopentadienyls, and $N(R_5)_2$ wherein $R_5$ has the same meaning as $R_1$, $R_2$, $R_3$ and $R_4$ and their fluorine, oxygen and nitrogen substituted analogs;

R is a monodentate or polydentate ligand selected from the group consisting of, hydrides, amides, azides, nitrates, cyclopentadienyls, and $N(R_5)_2$ wherein $R_5$ has the same meaning as $R_1$, $R_2$, $R_3$ and $R_4$ and their fluorine, oxygen and nitrogen substituted analogs; and m and n are positive numbers wherein m+n=v.

10. The precursor of claim 9 wherein M is selected from zirconium and hafnium.

11. The precursor of claim 10 wherein $R_1$ $R_2$ and $R_3$ are methyl or ethyl.

12. The precursor of claim 11 wherein R is t-butoxy and $R_1$ $R_2$ and $R_3$ are ethyl.

13. A process for preparing a metal siloxide precursor complex which is represented by the empirical formula:

$$(R)_mM\text{---}(O\text{---}SiR_1R_2R_3)_n$$

wherein M is a metal having a valence number v and selected from Zr, Hf, Sc, Y, La, Ce, Pr, Nd, Sm, Eu, Gd, Tb, Dy, Ho, Er, Tm, Yb, and Lu; $R_1$, $R_2$, and $R_3$, and $R_4$ are each independently monodentate or polydentate ligands selected from $C_{1-8}$ alkyl, $C_{1-8}$ alkoxides, benzyl, halides, hydrides, amides, azides, nitrates, cyclopentadienyls, and $N(R_5)_2$ wherein $R_5$ has the same meaning as $R_1$, $R_2$, $R_3$ and $R_4$ and their fluorine, oxygen and nitrogen substituted analogs; R is a monodentate or polydentate ligand selected from hydrides, amides, azides, nitrates, cyclopentadienyls and $N(R_5)_2$ wherein $R_5$ has the same meaning as $R_1$, $R_2$, $R_3$ and $R_4$ and their fluorine, oxygen and nitrogen substituted analogs; and m and n are positive numbers wherein m+n=v, the process comprising: reacting a metal complex of the formula $M(OR)_4$ where R has the meaning recited above with a silanol of the formula HO—Si—$R_1 R_2 R_3$ wherein $R_1 R_2$ and $R_3$ have the meanings recited above.

14. A process for preparing a metal silyl-amide precursor which is represented by the empirical formula:

$(R)_m M-[N-(SiR_1R_2R_3)_y(R_4)_{2-y}]_n$ wherein M is a metal having a valence number v and selected from the group consisting of Zr, Hf, Sc, Y, La, Ce, Pr, Nd, Sm, Eu, Gd, Tb, Dy, Ho, Er, Tm, Yb, and Lu; $R_1$, $R_2$, $R_3$, and $R_4$ are each independently monodentate or polydentate ligands selected from the group consisting of $C_{1-8}$ alkyl, $C_{1-8}$ alkoxides, benzyl, halides, hydrides, amides, azides, nitrates, cyclopentadienyls, a β-diketonate, and $N(R_5)_2$ wherein $R_5$ has the same meaning as $R_1$, $R_2$, $R_3$ and $R_4$ and their fluorine, oxygen and nitrogen substituted analogs; R is a monodentate or polydentate ligand comprising $C_{1-8}$ alkoxides; y is either 1 or 2; and m and n are positive numbers wherein m+n=v, the process comprising: reacting a metal complex of the formula $M(R)_4$ where R has the meaning recited above with a silyl amine having the formula $HN(Si R_1 R_2 R_3)_2$, $H_2N(Si R_1 R_2 R_3)$, or $HNR_4(SiR_1 R_2 R_3)$ wherein $R_1$, $R_2$, $R_3$, and $R_4$ have the meanings recited above.

15. A metal silyl-amide precursor which is composed of a complex represented by the empirical formula:

$(R)_m M-[N-(SiR_1R_2R_3)_y(R_4)_{2-y}]_n$ wherein M is a metal having a valence number v and selected from Zr, Hf, Sc, Y, La, Ce, Pr, Nd, Sm, Eu, Gd, Tb, Dy, Ho, Er, Tm, Yb, and Lu;

$R_1$, $R_2$, $R_3$, and $R_4$ are each independently monodentate or polydentate ligands selected from $C_{1-8}$ alkyl, $C_{1-8}$ alkoxides, benzyl, halides, hydrides, amides, azides, nitrates, cyclopentadienyls, a β-diketonate, and $N(R_5)_2$ wherein $R_5$ has the same meaning as $R_1$, $R_2$, $R_3$ and $R_4$ and their fluorine, oxygen and nitrogen substituted analogs;

R is a monodentate or polydentate ligand selected from $C_{1-8}$ alkoxides, hydrides, amides, azides, nitrates, a β-diketonate, and $N(R_5)_2$ wherein $R_5$ has the same meaning as $R_1$, $R_2$, $R_3$ and $R_4$ and their fluorine, oxygen and nitrogen substituted analogs;

y is either 1 or 2; and m and n are positive numbers wherein m+n=v.

* * * * *